United States Patent [19]

Vanharanta

[11] Patent Number: 5,458,119
[45] Date of Patent: Oct. 17, 1995

[54] VIBRATOR FOR DIAGNOSING JOINT DISORDERS

[75] Inventor: Heikki Vanharanta, Helsinki, Finland

[73] Assignee: Texas Back Institute, Plano, Tex.

[21] Appl. No.: 140,546

[22] Filed: Oct. 25, 1993

[51] Int. Cl.$^6$ ............................................. A61B 19/00
[52] U.S. Cl. ........................ 128/744; 128/781; 601/46
[58] Field of Search ........................ 128/739, 744, 128/774, 781; 601/46, 48

[56] References Cited

U.S. PATENT DOCUMENTS

| | | | |
|---|---|---|---|
| 3,822,708 | 7/1974 | Zilber . | |
| 3,868,951 | 3/1975 | Albrecht . | |
| 4,266,536 | 5/1981 | Casares | 128/57 |
| 4,347,838 | 9/1982 | McCauley | 128/33 |
| 4,475,401 | 10/1984 | Punia et al. | 73/658 |
| 4,476,873 | 10/1984 | Sorenson et al. | 128/660 |
| 4,632,095 | 12/1986 | Libin | 601/46 |
| 4,669,452 | 6/1987 | Osawa | 601/46 |
| 4,723,557 | 2/1988 | Gross | 128/787 |
| 4,964,412 | 10/1990 | Kelly | 128/744 |

FOREIGN PATENT DOCUMENTS

| | | | |
|---|---|---|---|
| 2652499 | 4/1991 | France | 601/48 |

OTHER PUBLICATIONS

"Bony Vibration Stimulation: A New, Non-Invasive Method . . . ", Math et al. Soc. for Back Pain Research Abstracts Oct. 30, 1992.

"Lumbar Disography In Normal Subjects", Walsh et al. Jnl. of Bone & Jt. Surgery Aug. 1990.

"The Relationship . . . CT/Discography", Vanharent et al. Spine Jan. 1987.

"Anatomy & . . . Spinal Pain", Weinstein, The Adult Spine Jan. 1991.

*Primary Examiner*—Max Hindenburg
*Attorney, Agent, or Firm*—Susan Weinhoffer-Zogbi

[57] ABSTRACT

The present invention is for a non-invasive pain provocative means for diagnosing spinal disorders. The device is a hand-held instrument which can be used in any doctor's office to differentiate which intervertebral disc is responsible for a patient's symptoms. The device produces pain by applying vibrations to the spinous process above a degenerated disc. The device has a handle for a user to easily grip, a vibration means located within the handle, and a detachable applicator positioned distally on the handle. The applicator, having many embodiments, is the element of the device which is applied to the patient's spine, in particular, to the spinous processes of the spine. This device can be useful in predicting a problem before an acute episode occurs or in staging the disc degeneration process or in screening people for certain jobs that have a high incidence of disc injury or trauma. The device can also be used for diagnosing joint problems for any synovial joint utilizing the same device and similar methodology. The invention, therefore, provides a very simple and economical device for diagnosing joint disorders without being invasive.

13 Claims, 4 Drawing Sheets

A

B

C

D

5,458,119

VIBRATOR FOR DIAGNOSING JOINT DISORDERS

BACKGROUND OF THE DISCLOSURE

The present invention generally relates to the devices that diagnose joint disorders. Specifically, the present invention provides a non-invasive pain provocative means for diagnosing spinal disorders utilizing vibration. This device was first presented at the Society for Back Pain Research on Oct. 30, 1992 in London, England.

The functional spinal unit of the spine is innervated with nerve fibers originating in the spinal cord. Two types of peripheral nerve fibers exist; myelinated and unmyelinated. Myelinated nerve fibers sense tissue or joint position and pressure. Therefore, they are mechanical receptors. Unmyelinated nerve fibers are mainly chemical and nociceptor receptors. By stimulating these nerve fibers, pain can be provoked.

The knowledge gained from disc innervation has changed the earlier concepts of the production of low back pain. Today nerve root compression is not regarded as the only source of such pain but it may also be attributable to intradiscal ruptures of the annulus, which have been found in many different lumbar syndromes. However, there is no simple tool available for the identification of these intradiscal ruptures in the patients examined, and can thus not be distinguished from other causes of back pain. The only possible method is discography that has to be performed under fluoroscopy which is laborious and expensive. In addition, it is not feasible for discography to be performed in everyday medical practice. A normal disc is painless in discography, but a close correlation has been found between annular rupture of a disc and reproduction of clinical pain.

Discography may be the most controversial diagnostic procedure for patients with low back pain. It involves the injection of radiographic contrast into the nucleus of an intervertebral disc. During the injection, the physician performing the procedure asks the patient if the injection generates pain similar to his/her "usual pain." This method of pain provocation is the only method at this time that can differentiate which disc is responsible for a patient's symptoms. However, discography requires premedication, x-ray control with needle injections, and a possibility of developing discitis. A non-invasive method of differentiating which disc is responsible for a patient's symptoms is needed.

Many radiographic diagnostic tools are used by the physician including plain radiographs, computer tomography scans, magnetic resonance imaging, bone scans, and myelograms. These tools image the spine and show potential sources of pain, but do not pinpoint the place of pain origin. Also, these tests demonstrate abnormalities in persons without pain, thus making pain provocation even more important.

Prior art for this device takes two forms, spinal diagnostic devices and devices for the spine utilizing vibration. U.S. Pat. No. 4,723,557 discloses a lordosimeter to diagnose lordosis and scoliosis. U.S. Pat. No. 4,476,873 discloses an ultrasound imaging system for scoliosis diagnosis. These two patents disclose methods and devices to diagnose spinal disorders that involve spinal misalignment. Whereas, the present invention can be used to diagnose the origin of back pain. U.S. Pat. No. 4,266,536 discloses a massaging device capable of being used by the person receiving the massage. U.S. Pat. No. 4,230,098 discloses a traction device capable of treatment with vibration. U.S. Pat. No. 4,347,838 discloses a foot massager with a special spinal roller attachment. All of the above patents treat the muscles of the back with a massaging action providing benefit and comfort. Whereas, the present invention uses vibration to provocatively produce pain which can be used to diagnose spinal disorders.

SUMMARY OF THE INVENTION

The present invention is for a non-invasive pain provocative means for diagnosing spinal disorders. The device is a hand-held instrument which can be used in any doctor's office to differentiate which intervertebral disc is responsible for a patient's symptoms. The device produces pain by applying vibrations to the spinous process in a degenerated disc. The device has a handle for a user to easily grip, a vibration means located within the handle, and a detachable applicator positioned distally on the handle. The applicator, having many embodiments, is the element of the device which is applied to the patient's spine; in particular, to the spinous processes of the spine. This device can be useful in predicting a problem before an acute episode occurs or in staging the disc degeneration process or in screening people for certain jobs that have a high incidence of disc injury or trauma.

The device can also be used for diagnosing joint problems for any synovial joint utilizing the same device and similar methodology. The invention therefore provides a very simple and economical device for diagnosing joint disorders without being invasive.

BRIEF DESCRIPTION OF THE DRAWINGS

Further advantages of the invention will become apparent from the subsequent description of embodiments in conjunction with the accompanying drawings. In the drawings.

DESCRIPTION OF THE PREFERRED EMBODIMENT

Figure 1:
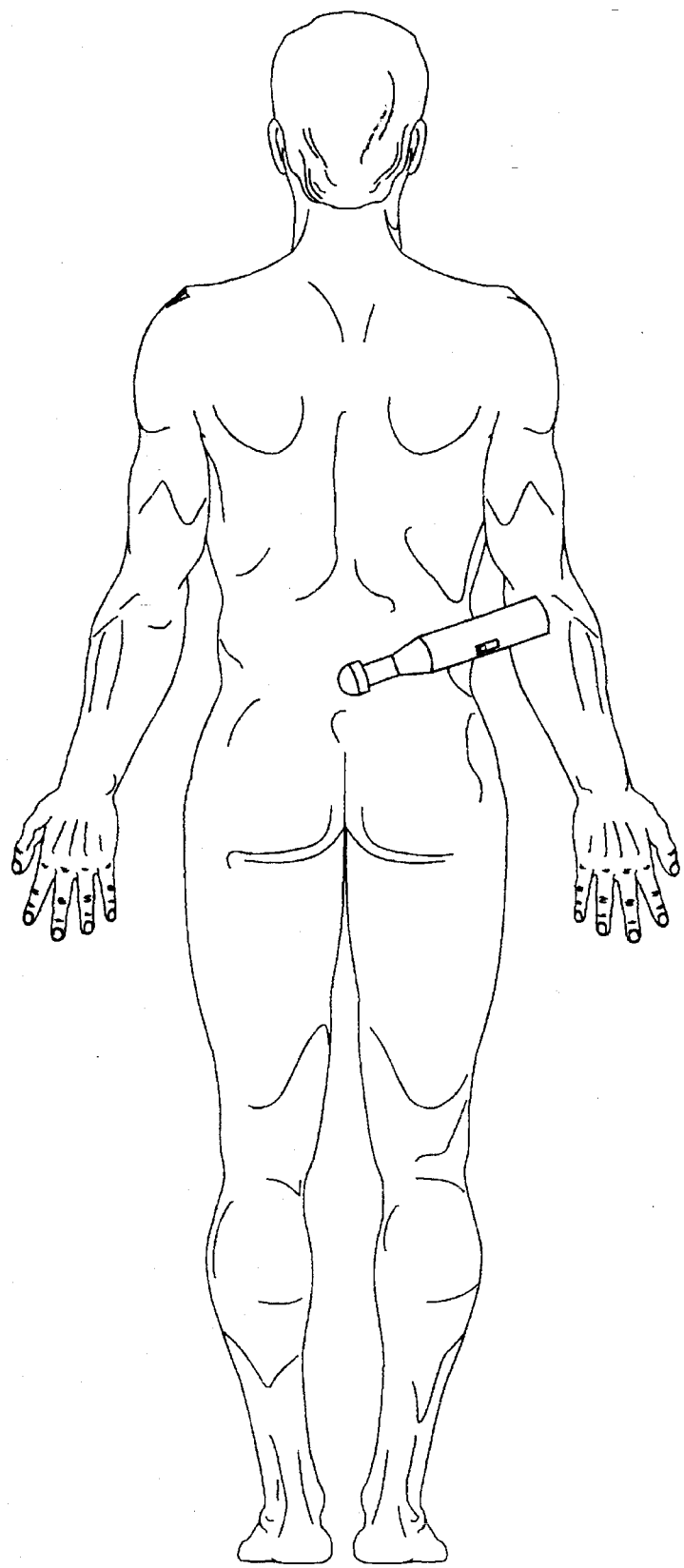
FIG. 1 is a schematic illustration of the joint vibrator in use on a person's back.
Figure 2:
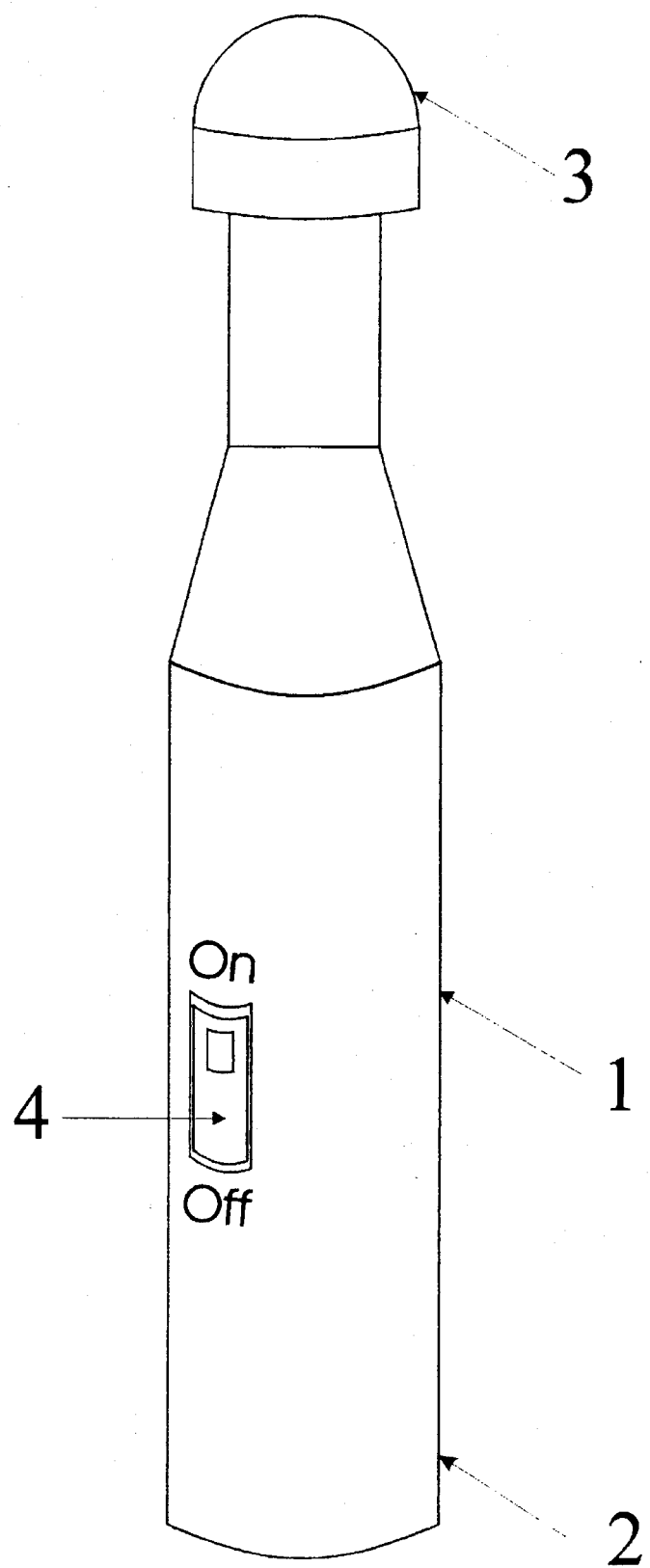
FIG. 2 is a perspective view of the joint vibrator.

FIG. 1 schematically illustrates the joint vibrator in use on a person's back. In FIG. 2 the joint vibrator comprises an easy to grip handle 1, a vibration means 2 which can be located within the handle as illustrated or outside the handle, and a detachable applicator 3. An on/off switch 4 may be added, but is not essential to the practice of the invention. Control switches for frequency, amplitude, and duty cycle may also be added, but are not illustrated in the drawings.

The material of construction of the handle is not critical and materials such as plastic, metal, or wood, could be used. The vibration means may be any suitable vibratory source. Through practice, we have found the frequency range of 40–60 Hz; and in particular 45–50 Hz, adequate to provoke a pain response in a joint. However, the frequency needed is dependent upon the mechanical attributes of the joint tested; for example, patient size and age. Therefore, frequencies outside of this range may be necessary to provoke a pain response. The vibratory source can be located within the housing for ease of use. However, this is not essential to the practice of the invention.

Figure 3:
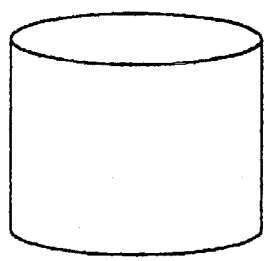
FIG. 3 is a perspective view of the tip embodiments.
Figure 3:
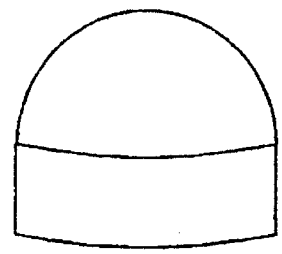
Figure 3:
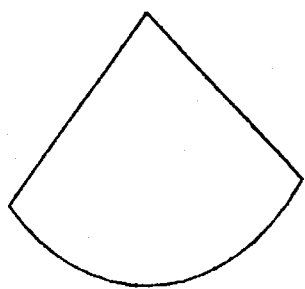
Figure 3:
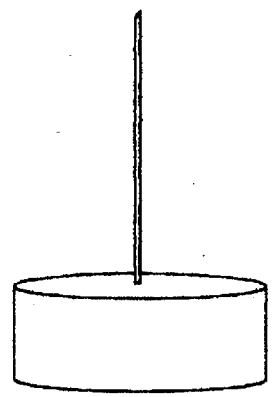
Figure 4:
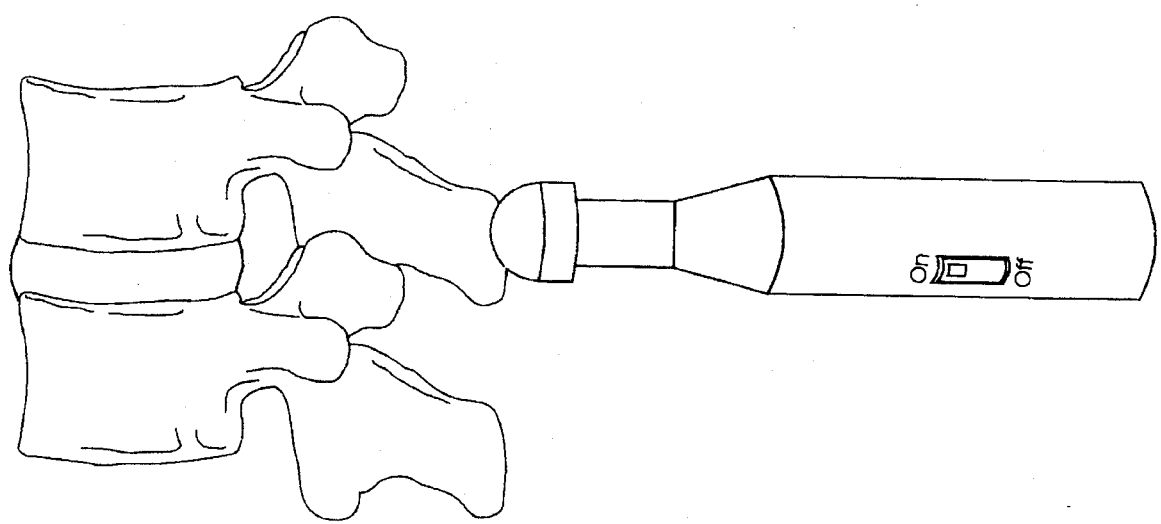
FIG. 4 is a schematic illustration of the joint vibrator and its point of application on the spinous process.

FIG. 3 illustrates the applicator embodiments: an end which is smooth and flat 3A, an end which is smooth and arcuate 3B, an end with a tapered tip 3C, and an end with a needle attached for invasive use 3D. The material construction of the tip is not critical and materials such as rubber, plastic, wood, or metal could be used. The applicator is detachable so that the end can be cleaned for each person's use and for the exchanging of applicator tip embodiments.

Once the appropriate tip is attached to the handle, the joint to be tested should be determined. Concerning the spine, the spinous processes above the disc level to be tested should be marked for the procedure. More than one level of the spine can be tested sequentially. The patient should lie prone or on his/her side with his/her back bare. The clinician using the device should locate the appropriate spinous processes to be tested. Each spinous process tested vibrates the disc level below; therefore, to test the L3–4 intervertebral disc, the L3 spinous process should be vibrated. The clinician places the applicator of the device on the appropriate spinous process and compresses the spine. Then, he/she vibrates the device for 2–5 seconds. The clinician then asks the patient if the vibration generated pain was different from any pain generated with just compression and if the pain was similar to his/her "usual pain". Once this is established, another level can be tested.

This device can be used to differentiate which disc is producing a patient's pain as does discography, without being an invasive procedure. The device has been shown to be very effective on patient groups when patients with previously operated backs, and painful prolapsed discs were excluded. Prolapsed discs were found to always be painless with vibration; although, they are found to be painful with discography. Previously operated backs almost always feel that the vibration is painful.

Evidently by combining information of vibration with the different imaging modalities (plain radiographs, MRI, CT), much more relevant information can be obtained from the origin of the back pain than by only examining the images.

The present embodiments of this invention are thus to be considered in all respects as illustrative and not restrictive. All changes which come within the meaning and range of equivalency of the claims, therefore, are intended to be embraced therein.

I claim:

1. A device for diagnosing spinal disorders utilizing non-invasive pain provocation means comprising:
   a housing including a head at one end and a handle at an opposite end wherein said housing has a hollow interior,
   a vibration means positioned within said housing and operatively coupled to said head,
   an application means detachably positioned on said head wherein said application means is approximately 5–20 mm in diameter, whereby the application means is applied to a spinous process of the vertebra and vibrated, thereby provoking a pain response.

2. The diagnostic device of claim 1 wherein the application means comprises two ends, wherein the first end is attached to the head of the housing and the second end is smooth and flat.

3. The diagnostic device of claim 1 wherein the application means comprises two ends, wherein the first end is attached to the head of the housing and the second end is smooth and arcuate.

4. The diagnostic device of claim 1 wherein the application means comprises two ends, wherein the first end is attached to the head of the housing and the second end is a tapered tip.

5. The diagnostic device of claim 1 wherein the application means comprises two ends, wherein the first end is detachably attached to the head of the housing and the second end is a needle.

6. The diagnostic device of claim 1 wherein a vibration frequency range is 40–60 Hz.

7. A method for diagnosing spinal disorders utilizing non-invasive pain provocation means comprising the steps:
   a) have the patient lie prone or on his/her side with back bare;
   b) locate the spinous process to be tested;
   c) place a vibrator's applicator on the spinous process indicated and compress;
   d) vibrate a device;
   e) ask the patient if the vibration-generated pain was different from that caused by compression and was the pain similar to his/her "usual pain"; and
   f) repeat on other levels if necessary.

8. A device for diagnosing joint disorders utilizing non-invasive pain provocation means comprising:
   a housing including a head at one end and a handle at an opposite end wherein said housing has a hollow interior,
   a vibration means positioned within said housing and operatively coupled to said head,
   an application means detachably positioned on said head wherein said application means is approximately 5–20 mm in diameter, whereby the application means is applied to a joint and vibrated, thereby provoking a pain response.

9. The diagnostic device of claim 8 wherein the application means comprises two ends, wherein the first end is attached to the head of the housing and the second end is smooth and flat.

10. The diagnostic device of claim 8 wherein the application means comprises two ends, wherein the first end is attached to the head of the housing and the second end is smooth and arcuate.

11. The diagnostic device of claim 8 wherein the application means comprises two ends, wherein the first end is attached to the head of the housing and the second end is a tapered tip.

12. The diagnostic device of claim 8 wherein the application means comprises two ends, wherein the first end is detachably attached to the head of the housing and the second end is a needle.

13. The diagnostic device of claim 8 wherein a vibration frequency range is 40–60 Hz.

* * * * *

UNITED STATES PATENT AND TRADEMARK OFFICE
CERTIFICATE OF CORRECTION

PATENT NO. : 5,458,119
DATED : October 17, 1995
INVENTOR(S) : Heikki Vanharanta

It is certified that error appears in the above-indentified patent and that said Letters Patent is hereby corrected as shown below:

On the title page, item [75], should read as follows:

Inventor: Heikki Vanharanta, Helsinki, Finland
and Matti Yrjämä, Vaala, Finland

Signed and Sealed this

Twenty-sixth Day of March, 1996

Attest:

BRUCE LEHMAN

Attesting Officer     Commissioner of Patents and Trademarks